United States Patent [19]

Wyatt

[11] Patent Number: 4,615,679
[45] Date of Patent: Oct. 7, 1986

[54] LIGHT SHIELD FOR USE WITH LIGHT CURING APPARATUS

[76] Inventor: Thomas K. Wyatt, 99 Kilroy Way, Atherton, Calif. 94025

[21] Appl. No.: 741,253

[22] Filed: Jun. 3, 1985

[51] Int. Cl.⁴ .............................................. A61C 5/04
[52] U.S. Cl. ................................................. 433/229
[58] Field of Search ................... 285/177; 433/229, 29

[56] References Cited

U.S. PATENT DOCUMENTS 2,025,067  12/1935  Miller .................................. 285/177
4,445,858  5/1984  Johnson .............................. 433/229

*Primary Examiner*—Robert Peshock
*Attorney, Agent, or Firm*—Flehr, Hohbach, Test, Albritton & Herbert

[57] ABSTRACT

A light shield device shields radiation used for curing composites during dental restoration. The device is configured to include a clamping section with variable clamping diameters and a tapered shielding section. The device is formed with a material that allows a tight frictional engagement with a curing light gun.

4 Claims, 3 Drawing Figures

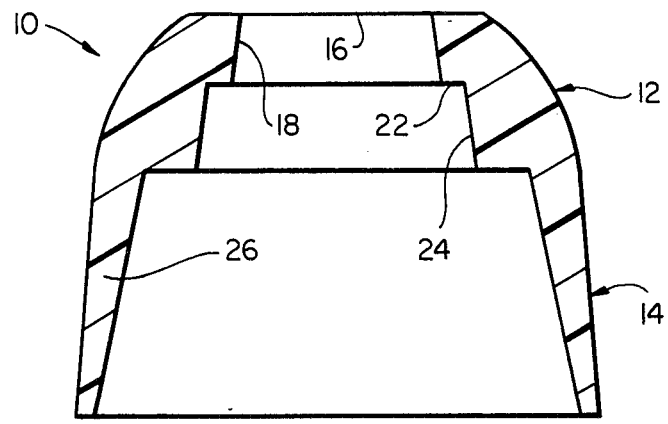
FIG_1
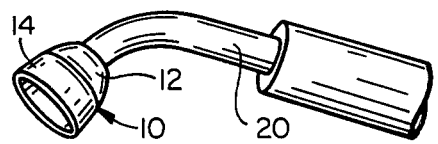
FIG_2
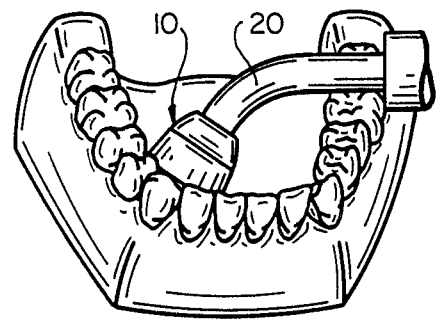
FIG_3

LIGHT SHIELD FOR USE WITH LIGHT CURING APPARATUS

DESCRIPTION

Technical Field

This invention relates to a light shielding device for use with light curing apparatus employed for dental restoration.

Background Art

In the process of forming veneers on teeth requiring restoration, composite resin materials are applied and cured by application of light of a selected wavelength. Previously ultraviolet light was employed to effectuate such curing, but it was recognized that ultraviolet radiation is harmful to human skin and eye tissues. As a result, visible light curing units were developed and it was generally believed that the problem of harmful radiation effects had been obviated.

The wavelength of light employed by such visible light curing units used to polymerize composite resins is in the range of about 460–480 nanometers, which is extremely damaging to the human eye. This spectrum of visible light contains a component designated as "blue light." Blue light will cause retinal burns after very short exposures of less than one second. As the time of exposure is increased, the burns become more severe. This damage is called solar retinitis. Retinal burns appear 48 hours after light exposure, and although healing occurs in 20–30 days, the healed areas experience permanently degenerative tissues. This damage to the retina is irreparable, and the damaged rod and cone photoreceptors cannot be regenerated.

It is known that 510 nanometers is considered the minimal cutoff point for severe eye damage. Shorter wavelengths, as those essential to cure composite resins, are much more dangerous than longer wavelengths. For example, a wavelength of 441 nanometers is 2.5 times more damaging than 488 nanometers.

Extended exposure to very low levels of blue light at 463 nm., the same wavelength used to cure composites, can cause permanent blue blindness. Repeated exposures to very low levels of blue light can produce retinal injury.

In most situations in dental clinics, the blue light that reaches the eyes is reflected light. Although some scientists feel that reflected light is less harmful to the eye than direct light, the recommendation is to use eye protection to screen both direct and reflected light. This protection has been implemented in various ways which may not be totally effective. For example, the dental clinician may cover the curing field of the applied light with the reflective side of a mouth mirror in order to reflect the light against the restorative area to improve curing. In other cases, optical glasses are used in order to look at the lamp source for proper placement against the tooth. However, most optical glasses transmit blue light and near ultraviolet light radiation with minimal attenuation. These approaches suffer from awkwardness and affect the efficiency of the dental clinician, as well as being harmful and dangerous to the eyes of the patient and the clinician.

It would be desirable to have a simple and effective means to shield the harmful radiation from the eyes of the patient and the operating clinician which can be expediently used in combination with the light curing apparatus.

SUMMARY OF THE INVENTION

An object of this invention is to provide a light shielding device that effectively blocks harmful radiation, which is used for curing composite resins during dental treatment, from damaging the eyes of those persons in the vicinity of the harmful radiation.

In accordance with this invention a light shield device that is used in conjunction with a light curing apparatus for polymerizing composite resins is formed as an integral unit, preferably in a truncated parabolic type shape. The device includes a clamping section at one end and a shielding section at the other end. The clamping section affords different diameters that allows engagement of the light shield device with different diameter tubings of light curing apparatus from which the curing light emanates. The material of the shielding device is expandable when heated, and constricts when cooled after heating. The shielding section allows the curing radiation to impact the limited area of the composite resin while blocking the escape and divergence of harmful radiation to other areas and objects, such as human eyes, in the vicinity of the radiation.

BRIEF DESCRIPTION OF THE DRAWINGS

The invention will be described with reference to the drawings in which:

FIG. 1 is a schematic sectional view of the light shield device of this invention;

FIG. 2 is a plan view of the tube portion of the visible light apparatus, on which the shield device of this invention is mounted; and FIG. 3 illustrates the application of the light curing apparatus, with the mounted shield of this invention, to a model tooth.

DESCRIPTION OF THE PREFERRED EMBODIMENT

With reference to FIGS. 1–3, a light shield device 10 is formed in a substantially truncated parabolic type configuration including a clamping section 12 and a shielding section 14. The clamping section has an aperture 16 encompassed by an annular portion 18. The aperture 16 has a predetermined diameter that affords a tight fit frictional engagement with a light gun tube 20 of a given diameter which supplies "blue light" radiation. The light gun tube encloses fiber optic elements that conduct the light generated by the radiation source of the light curing apparatus. In present day practice, visible blue light is employed during dental treatment when reconstructing a tooth to polymerize and cure composite resins that are applied to the tooth under treatment. As described heretofore, the wavelength and very high intensity of the blue light are such that severe retinal damage would be experienced if the light is received and impacted on the photosensor elements of the eye.

At present, the light curing guns, which generally operate with tungsten halogen light sources, are provided with various diameters and different shapes of light gun tubings. The light shield device of this invention is formed to engage virtually any diameter. As depicted in FIG. 1, the small diameter annulus 18 is provided at the end of the clamping section. The light shield device has a step 22 to a second annular portion 24 of larger diameter than the first annular portion 18 which allows accommodating the shield device to a light gun tube of larger diameter. To accommodate a larger diameter gun, the light shield device is reamed to remove the smaller annular portion 18 so that the larger annular portion 20 becomes the top end section for engaging the larger diameter gun tube.

In accordance with the preferred embodiment of this invention, the light shield device is made of a material that stretches easily when heated, and then shrinks to its former normal shape when cooled. In practice, the light shield device having the aperture of desired diameter is inserted into hot water, thereby expanding the aperture to allow mounting the shield device to the tube 20 at the light emanating end of the light gun. As the material of the shield device cools, it constricts and forms a tight fit around the light gun tube so that it is effectively locked in place and will not slip.

The shielding section 14 projects past the tip of the light gun tube so that it blocks divergence of the blue light and thereby prevents harmful radiation from reaching the eye of the patient or the dental clinician. The extended shielding section also acts as a depth stop and prevents contact between the tip of the light gun tube and the tooth surface which prevents potential thermal damage to approximating pulp tissues. The shielding section has a tapered portion 26 to provide greater flexibility for applying the light source to working areas of the tooth surface.

The material used for the light shield device needs to be flexible, stretchable, resilient and tough enough to withstand use in the dental reconstruction environment. To this end, a preferred material used for the light shield device is Dupont Elvax 460 (Trademark of Dupont Corp.), which is a clear resin material. The material is composed of a copolymer of ethylene and vinyl acetate, and is mixed with a coloring agent prior to forming the configured light shield device. The light shield material is nonreflective thus preventing reflection and dispersion of the blue light during operation of the light curing gun apparatus.

The light shield device is relatively inexpensive when compared to previous devices used for shielding purposes, and may be disposable or sterilized for repeated use. Although the preferred implementation employs the aforementioned Dupont Elvax 460 composition, other materials can be used, such as polyvinyl chloride.

In the specific implementation disclosed herein, the diameters of the apertures for the annular section 18 and annular section 24 are 6.0 millimeters and 8.0 millimeters respectively, and the diameter of the aperture of the tapered working section at the opposite end is 16.0 millimeters. Typical dimensions are illustrated in FIG. 1, but it should be understood that variations and modifications in dimensions, shape and material may be made within the scope of the invention.

What is claimed is:

1. A removable and replaceable integral light shield device for use with a light gun having an extending tubular part with an end from which polymer curing blue light radiation is applied to a tooth under treatment comprising:
    a clamping section for tight frictional engagement with said tubular part of said light gun; and
    a working section for shielding the radiation from impacting the eyes of individuals in the vicinity of such radiation and for limiting the radiation path to the area of the tooth under treatment;
    wherein said clamping section includes a first annular portion of a given diameter and a second annular portion of larger diameter than said given diameter for engaging tubular parts of different diameters respectively, said light shield device being made from a flexible and resilient material which is stretched by heating and restored to its normal shape upon cooling.

2. A light shield device as in claim 1, having more than one annular portion of different diameters in a stepped progression, and wherein the smallest diameter annular portion is at the outermost portion of the clamping section and the diameters of the annular portions progressively increase.

3. A light shield device as in claim 1, wherein the material of said device is stretched when immersed in hot water and constricts to its normal size when removed from the water into ambient air.

4. A light shield device as in claim 3, wherein said device comprises a copolymer of ethylene and vinyl acetate.

* * * * *